US011938238B2

(12) United States Patent
Ismail

(10) Patent No.: US 11,938,238 B2
(45) Date of Patent: *Mar. 26, 2024

(54) DISINFECTION SYSTEM

(71) Applicant: Innovative Technologies, Waltham, MA (US)

(72) Inventor: Nassar Ismail, Dover, MA (US)

(73) Assignee: Innovative Technologies, Waltham, MA (US)

( * ) Notice: Subject to any disclaimer, the term of this patent is extended or adjusted under 35 U.S.C. 154(b) by 232 days.

This patent is subject to a terminal disclaimer.

(21) Appl. No.: 17/156,152

(22) Filed: Jan. 22, 2021

(65) Prior Publication Data

US 2021/0386885 A1    Dec. 16, 2021

Related U.S. Application Data

(63) Continuation of application No. 16/887,722, filed on Jun. 16, 2020, now Pat. No. 10,960,094.

(51) Int. Cl.
| | |
|---|---|
| *A61L 2/10* | (2006.01) |
| *A61B 1/00* | (2006.01) |
| *A61B 1/267* | (2006.01) |
| *A61L 2/20* | (2006.01) |
| *A61M 16/06* | (2006.01) |

(52) U.S. Cl.
CPC ............ *A61L 2/10* (2013.01); *A61B 1/00006* (2013.01); *A61B 1/00016* (2013.01); *A61B 1/00094* (2013.01); *A61B 1/0016* (2013.01); *A61B 1/00165* (2013.01); *A61B 1/0019* (2013.01); *A61B 1/2676* (2013.01); *A61L 2/202* (2013.01); *A61M 16/0666* (2013.01); *A61B 2505/05* (2013.01); *A61L 2202/121* (2013.01); *A61L 2202/24* (2013.01); *A61M 2210/1039* (2013.01)

(58) Field of Classification Search
CPC ........................................................ A61L 2/10
See application file for complete search history.

(56) References Cited

U.S. PATENT DOCUMENTS

| | | | |
|---|---|---|---|
| 4,095,113 | A | 6/1978 | Wolff |
| 5,165,395 | A | 11/1992 | Ricci |
| 6,497,480 | B1 | 12/2002 | Palestro |
| 6,638,216 | B1 | 10/2003 | Durell |
| 7,201,767 | B2 | 4/2007 | Bhullar |
| 7,409,954 | B2 | 8/2008 | Dobkine |
| 7,597,856 | B2 | 10/2009 | Naarup |
| 7,658,891 | B1 | 2/2010 | Barnes |
| 8,841,640 | B1 | 9/2014 | Abbott |

(Continued)

FOREIGN PATENT DOCUMENTS

| | | |
|---|---|---|
| CN | 105517614 | 4/2016 |
| EP | 2916061 A1 | 9/2015 |

(Continued)

*Primary Examiner* — Kevin Joyner
(74) *Attorney, Agent, or Firm* — Lambert Shortell & Connaughton; David J. Connaughton, Jr.; Justin P. Tinger

(57) ABSTRACT

A disinfection system is provided. The disinfection system may utilize ultraviolet light and/or ozone for disinfection of infected tissue. For example the system may involve an endoscopic ultraviolet light to disinfect lung tissue. In another aspect, the system may involve a ventilator which provides ozone in small doses to disinfect the tissue. Combinations and variations are further disclosed.

17 Claims, 14 Drawing Sheets

(56) References Cited

U.S. PATENT DOCUMENTS

| | | |
|---|---|---|
| 9,616,147 B2 | 4/2017 | Leyva |
| 10,092,355 B1 | 10/2018 | Hannaford et al. |
| 10,485,888 B2 | 11/2019 | Schmidt |
| 10,492,670 B1 | 12/2019 | Bendory et al. |
| 2003/0232303 A1 | 12/2003 | Black |
| 2006/0144690 A1 | 7/2006 | Fink |
| 2009/0205664 A1 | 8/2009 | Lyon |
| 2010/0168823 A1 | 7/2010 | Strisower |
| 2013/0030250 A1 | 1/2013 | Findeisen |
| 2014/0107496 A1 | 4/2014 | Hellstrom et al. |
| 2017/0189711 A1 | 7/2017 | Shur et al. |
| 2018/0042461 A1 | 2/2018 | Togino |
| 2018/0049911 A1* | 2/2018 | Alzeer ............... A61L 2/10 |
| 2019/0099050 A1* | 4/2019 | Kirschman ........... A61L 9/20 |
| 2019/0321499 A1* | 10/2019 | Igarashi ............ A47K 10/48 |
| 2021/0353794 A1* | 11/2021 | Popa-Simil ......... G06V 40/10 |

FOREIGN PATENT DOCUMENTS

| | | |
|---|---|---|
| ES | 2 654 845 | 2/2018 |
| JP | S5234587 A | 3/1981 |
| JP | 6669845 B1 | 3/2020 |
| KR | 2013 0034192 A | 4/2013 |
| WO | 2004095550 | 11/2004 |
| WO | 2018/089288 A1 | 5/2018 |
| WO | 2020198545 A1 | 10/2020 |
| WO | 2021249668 A1 | 12/2021 |
| WO | 2022147059 A1 | 7/2022 |
| WO | 2022184609 A1 | 9/2022 |

\* cited by examiner

DISINFECTION SYSTEM

BACKGROUND OF THE INVENTION

Field of the Invention

The present disclosure relates generally to disinfection devices which use ultraviolet radiation (hereinafter referred to a "UV light" or "ultraviolet light") and/or ozone. More particularly the present disclosure relates to a lung or other tissue disinfection system which provides treatment for infections in the lungs or tissue.

Description of Related Art

Many infectious diseases such as influenza, coronavirus, and other viruses and bacteria cause mortality and morbidity via respiratory infection. In some cases, this respiratory infection can progress to pneumonia, a leading cause of death and disability due to such infections. Currently, despite the massive advances is other areas of technology, viral pneumonia remains without any reliable treatment. At best, the current care relies on keeping a patient alive long enough for the body to develop antibodies and an immune response to fight of the disease on its own, or die.

Moreover, as the world becomes more interconnected and grows into wilderness areas, the risk of worldwide pandemic diseases has greatly increased. Such pandemics, including most recently, COVID-19, can devastate life as we know it, killing millions, forcing economic shut downs and forcing people into isolation. Therefore, effective treatments of these illnesses is of paramount importance to maintain our current way of life.

What is needed is a system which may aid in treatment of infected lungs/organs by disinfecting tissue, thereby aiding the body in its immune response to an infection.

SUMMARY

The subject matter of this application may involve, in some cases, interrelated products, alternative solutions to a particular problem, and/or a plurality of different uses of a single system or article.

In one aspect, an endoscope assembly is provided for disinfection of bodily tissue. The endoscope assembly has an ultraviolet ("UV") light source, such as a lamp, LED, or other light source, with a fiber optic cable connected thereto and extending along an endoscope to a distal end of the endoscope. This endoscope can be adjusted in position and direction/orientation along its length to allow it to be positioned within the lungs or other area of a patient, and to direct the UV light to various areas of tissue. Further, the endoscope has a mirror/lens attached to the endoscope near the distal end, the mirror being adjustable in position to direct UV light coming from the end of the endoscope. The endoscope also has a lens/mirror assembly attached near the end of the endoscope near the distal end. The lens/mirror assembly is adjustable in position to manipulate the UV light coming from the end of the endoscope.

In another aspect, a disinfecting ventilator is provided. The ventilator has an inspiratory line connected to an air source providing a pressurized gas flow. An ozone source is also connected to the inspiratory line to provide ozone to the lungs/organ of a patient. This ozone operates to disinfect tissue that it is exposed to, thereby facilitating healing of infected lungs and other air-accessible tissue.

DETAILED DESCRIPTION

Figure 1:
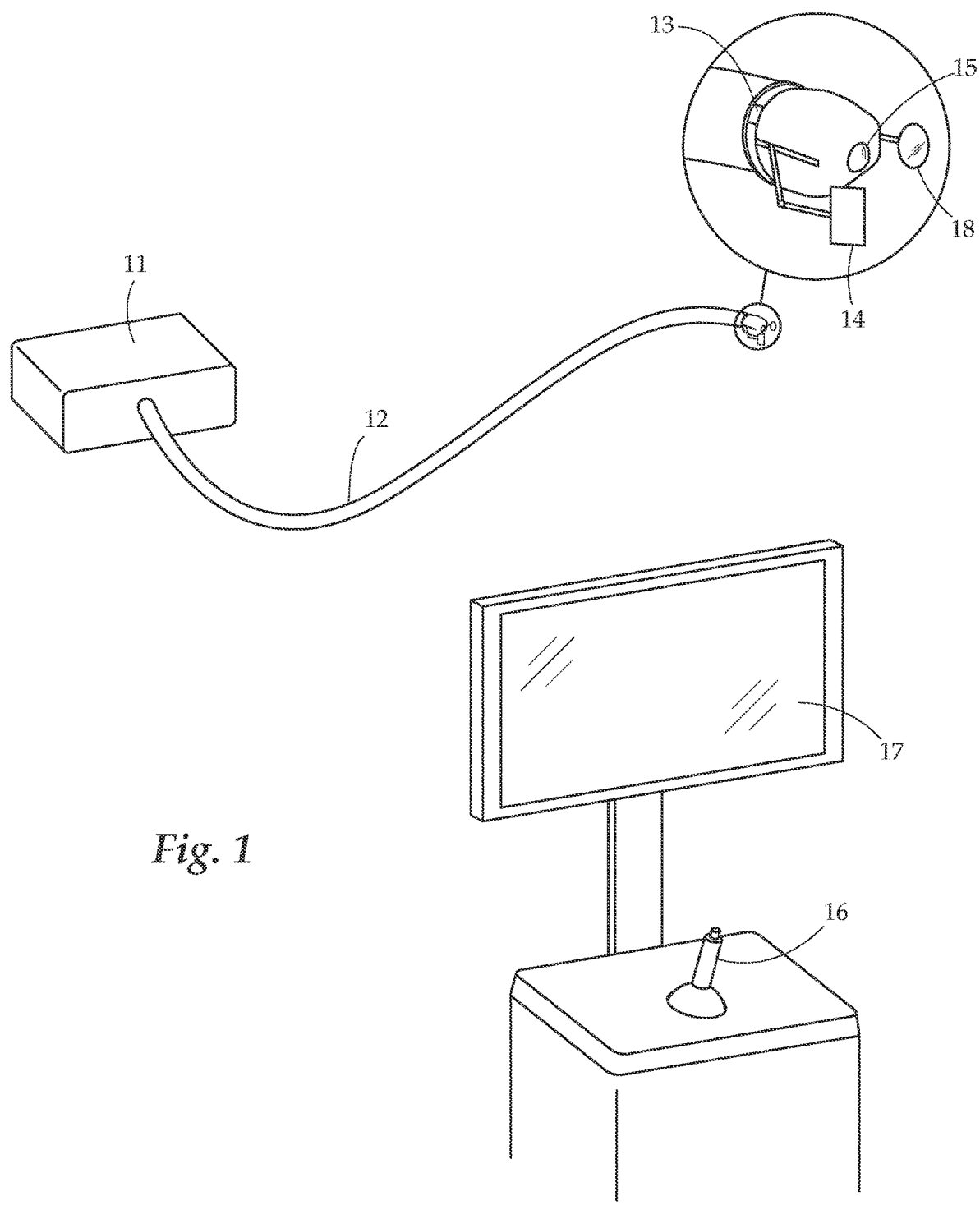
FIG. 1 provides a perspective view of an embodiment of the invention as well as a control system thereof.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

The present invention solves many problems of the prior art. The present disclosure relates to a new disinfection system which can be used to treat infected tissue in humans or animals. This invention focuses on sterilizing and/or disinfecting tissue, and in some cases also the fluid surrounding the tissue. In so doing, the tissue and tissue surrounding it, is more easily allowed to heal in a cleaner and less infected environment, and can be exposed to fresh/clean air and/or fluid. Further, disinfecting the tissue limits spread of the illness to healthy tissue. Thereby helping to isolate the infection, which allows the body to focus its efforts and not be overwhelmed by the infection. Embodiments are generally disclosed as applied to lung tissue treatment, however this invention is certainly not limited to lung tissue treatment, indeed it may be applied to any bodily tissue.

Ultraviolet (UV) light is known to kill viruses, bacteria, and fungus. Ozone is also a well-known gas which kills bacteria and viruses. Therefore, these two technologies, used alone or in combination, may be very useful for treatment of infected tissue and surrounding air and fluid. Allowing the tissue, and the rest of the body, to heal.

Generally, the present disclosure is related to systems and methods for disinfection. In one aspect, a endoscope having a fiber optic UV cable is provided. The endoscope allows for insertion into lungs or other portions of a body to direct UV light at tissue. Further, the endoscope is equipped with at least one of a mirror and/or lens system to precisely magnify, amplify, focus, and direct the UV light to specific tissue. In particular, lungs are formed of many branching bronchi, called the bronchial tree, with the bronchi become smaller and smaller as the tree progresses. For example, the third generation of the bronchial tree has a cross sectional width of just a few millimeters, with progressive generations becoming smaller still. The lungs, therefore, have many hard to reach areas. To reach these narrow, branched sections, the endoscope uses a mirror and/or lens assembly to create a narrow beam of UV light directed at the desired tissue area.

In another aspect, a ventilator or other air delivery system which provides ozone supplementation is provided. The ventilator is operable to provide small doses of ozone into the lungs, which in turn kills or deactivates pathogens such as viruses and bacteria. This ozone is provided in low doses which limits tissue damage, but still provides effective disinfection. The ventilator may be any type of oxygen/air supplementation system, such as a breathing mask, a face or nasal mask, nasal cannula, non-invasive ventilator, or invasive, intubation-type ventilator. Ozone may be provided by a low continuous flow, pulsed flow, periodic flow, and the like. Certain guidelines exist for safe ozone exposure, such as OSHA guidelines which provide: 0.2 ppm for no more than two hours; 0.1 ppm for 8 hours per day doing light work; 0.08 ppm for 8 hours per day doing moderate work; and 0.05 ppm for 8 hours per day exposure doing heavy work. Ozone may be provided by the ventilator in this range, or may be increased for shorter periods to provide greater disinfection, as can be directed by a doctor and tolerated by the individual. Depending on the severity of the patient's case, higher ozone levels may be tolerable as a last resort treatment. In one embodiment, the ventilator may provide only oxygen and ozone, limiting nitrogen exposure. In one embodiment, exhaled (expiratory) gas may be disinfected using UV and/or ozone treatment, thereby preventing spread of the infection to nearby doctors and healthy individuals.

Moreover, a combination of these two disinfecting system may be used. A combined system which includes a UV light source and endoscope as well as an ozone ventilator is contemplated. In such a system, the UV treatment may be supplemented with ozone to reach deep into the narrow recesses of the lungs in sequence or at the same time. Moreover, for an invasive ventilator, an endoscope may also be inserted into the lung simultaneously to provide UV light to the lungs while also providing ozone treatment. Similarly, the UV endoscope may optionally also include an ozone and oxygen tube which can apply ozone to tissue adjacent to the endoscope.

Turning now to FIG. 1, a view of an embodiment of the UV disinfecting endoscope assembly is provided. The endoscope has a UV light source 11. The UV light source 11 may be a laser or non-laser source. In certain embodiments, the UV light may be selected to have a particular wavelength(s) which does not damage human tissue but is lethal to pathogens such as viruses, bacteria, and fungi. For example, the UV wavelengths of the various embodiments disclosed herein may be between 100-400 nm. The UV light may also be selected to have a particular wavelength(s) which can penetrate through fluid such as water, lung fluid, and other bodily fluids. In still other embodiments, the UV light may be selected to have a wavelength which is absorbed by bodily fluid, so as to enhance fluid disinfection. In many embodiments, the UV light source 11 may be operable to generate or apply more than one wavelength, for disinfection of different materials. Optical or electronic filters may also be used to select a particular wavelength.

The generated UV light passes through the endoscope 12 via fiber optic cable which is connected to the UV source 11 and extends along the endoscope 12. At the distal end of the endoscope 12 is a light 15 where the UV light from the light source 11 exits from the end of the fiber optic cable. The endoscope 12 is adjustable in position and direction/orientation along its length. The endoscope has a mirror 14 which is independently movable in this embodiment via arm. The mirror arm may be adjustable in position and orientation and in some embodiments extendable via telescoping or other structure to thereby move mirror 14. The mirror 14 may be quite small in certain embodiments so as to allow it to fit into small areas of the lung tissue and to allow it to direct the light even further into the bronchi. In some embodiments, the mirror may be as small as approximately 1 mm in diameter.

The lens 18 may be a single lens or an assembly of a plurality of lenses. The lens 18 is independently movable via arm. The lens arm may be adjustable in position and orientation and in some embodiments extendable via telescoping or other structure to thereby move lens 18 or a lens assembly. In lens assembly embodiments, each lens may be independently movable, and may also include reflectors and/or mirrors. The lens 18 operates to collect, converge, diverge, focus, magnify, redirect, or otherwise manipulate light from the UV outlet 15. The lens 18 is movable so as to further control direction of the light emitted from the light 15. In certain embodiments, the lens 18 or lens assembly is able to collect the light into a very small beam. In one embodiment, the lens assembly may direct the UV light into a beam of approximately 0.5-5 mm in width so as to pass into common branches of the bronchial tree. Control of the endoscope 12 and its components is achieved, in this embodiment, by way of a computer 17 and joystick 16. Of course, other control known in the art, disclosed herein, or to be invented, may be used. Control of the endoscope and components may include anything from fully manual control to completely machine operated control, is contemplated as part of this invention. For an operator to view what is around the distal end of the endoscope, a fiber optic cable may provide for direct viewing, or a camera may be positioned at or near the distal end of the endoscope 12 to digitally record and transmit pictures of the surroundings of the endoscope, among other options. In one embodiment, a second endoscope may provide additional light and camera to view the inside of the lungs. The first and second endoscopes of this embodiment may, in some cases, enter the body through a single tube.

Figure 2:
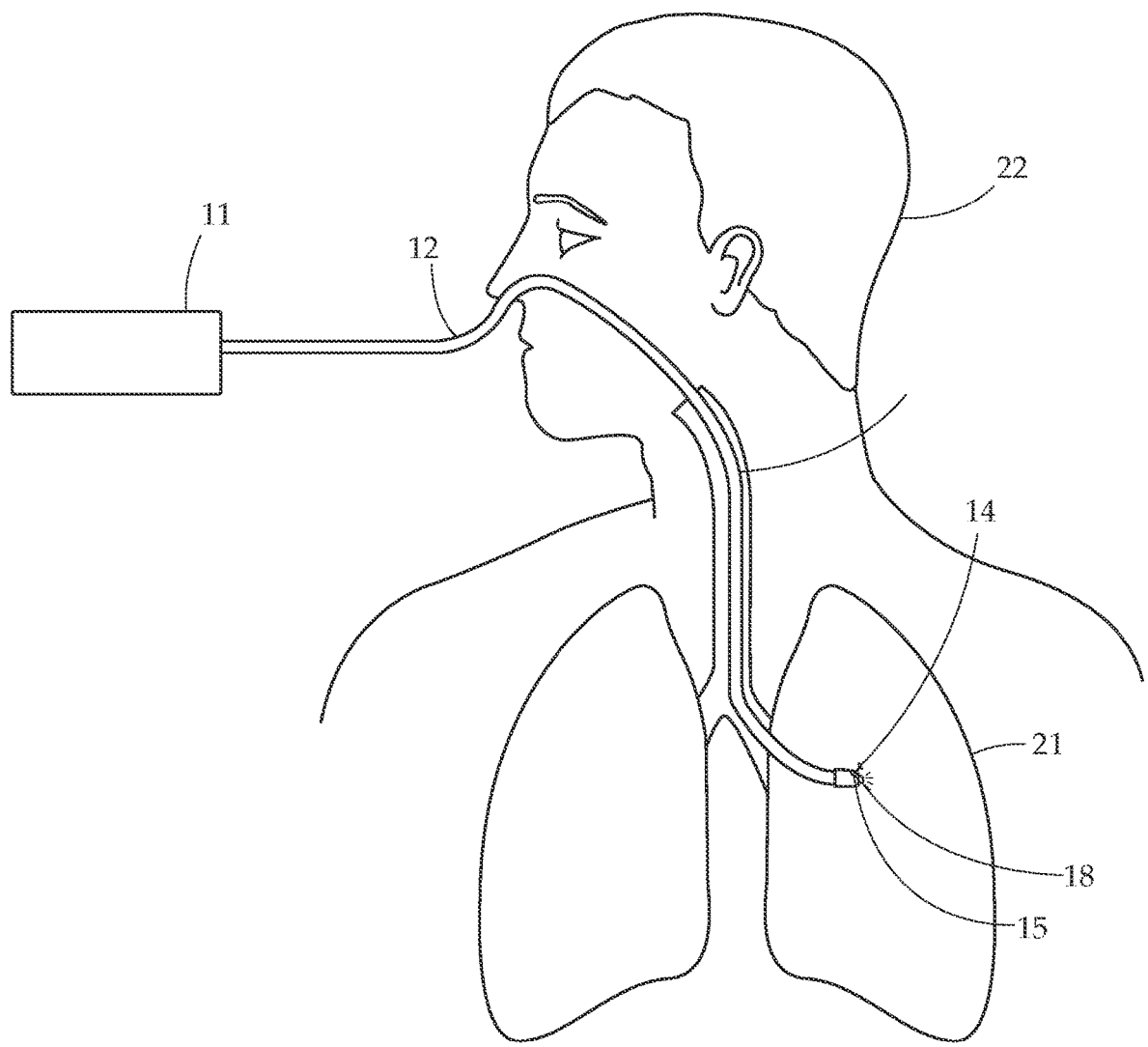
FIG. 2 provides a view of an embodiment of the present invention inserted into a lung of a patient.

As seen in FIG. 2, the endoscope of the present invention can be used as a bronchoscope to enter the lungs via, for example, the patient's nose. Once inserted, the UV light can be used to disinfect areas of the lung tissue and fluid within the lungs.

Figure 3:
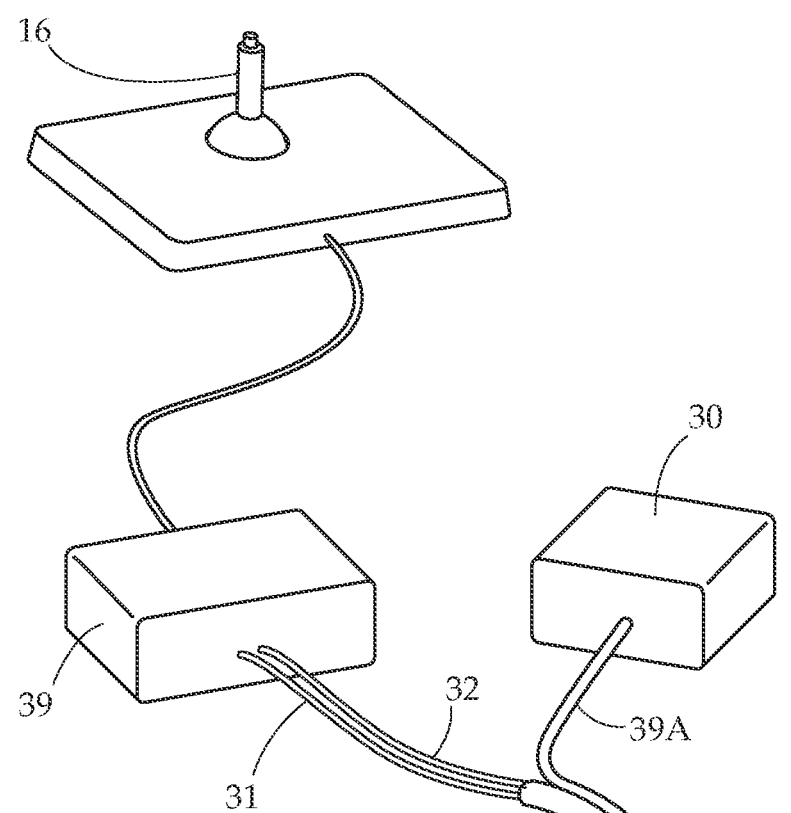
FIG. 3 provides a perspective view of another embodiment of the invention.
Figure 3:
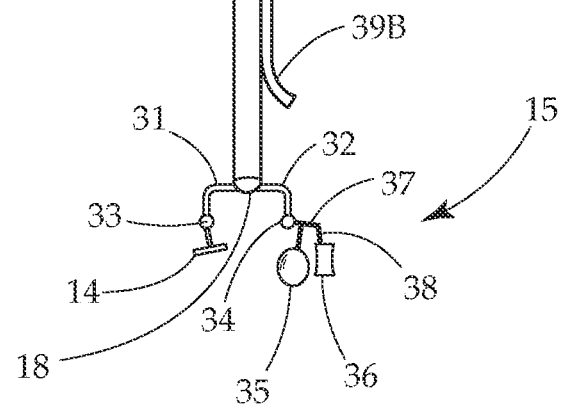

Turning now to FIG. 3, another embodiment of the endoscope is shown. In this view, the endoscope 12 has a light 18 at its distal end, with UV source (not shown) connected to its opposite end, as can be seen in FIG. 2, for example. Control of the direction of the endoscope, mirror 14, and lens assembly 15 is achieved in this embodiment by movement of cable 31 for the mirror 14 and cable 32 for the lens assembly 15. Cable 31 is controlled, in this embodiment, by one or more motorized controllers within the controller 39 which pull and push on the cable 31, which in turn pivots mirror 14 about hinge 33. Cable 32 is similarly moved to cause the mirror assembly 15 to pivot about hinge 34. In other embodiments, multiple cables may be used to move the mirror and/or assembly, adding more axes of motion including but not limited to horizontal and vertical directions. Similarly, multiple hinges, such as both a horizontal hinge and a vertical hinge, a ball and socket hinge, or multiple ball and socket hinges may be used to allow additional and differing movements of the mirror and lens/lens assembly.

Also in other embodiments, instead of a pushing and pulling of the cables 31, 32, two opposite cables may be used, with each being pullable to cause movement in opposite directions. For example, in one embodiment a first wire extends along a length of the endoscope to engage the mirror or lens/lens assembly via the vertical hinge, such that a movement of the first wire causes it to move via the vertical hinge, and a second wire extends along a length of the endoscope to engage the mirror or lens/lens assembly via the horizontal hinge, such that a movement of the second wire causes it to move via the horizontal hinge. Movement of the endoscope itself also can be used to manipulate the mirror and/or lens/lens assembly.

Of course, in other embodiments, direct motorized control is also possible to move the mirror 14 and lens assembly 15, movable with a flexible arm among any other movement structure capable of moving and changing the direction of the mirror 14 and lens assembly 15. Control of these components, in this embodiment, is achieved by the joystick 16 which controls the components of the motorized controller 39.

FIG. 3 further shows an embodiment of the disinfecting endoscope assembly having a suction tube 39B which may be fixed or independently controllable using known endoscope control mechanisms. The suction tube 39B connects to a suction device 30 such as a vacuum pump, low pressure source, fan, and the like. The suction tube 39B is operable to mechanically remove, via suction, infected or other fluid in the lungs. In certain embodiments, fluid within the lungs may become thinner once disinfected, and therefore is easier to remove using the suction tube 39B. In other embodiments, the suction tube 39B may be used to remove fluid before application of the UV light, to get fluid out of the way of the UV light, which may allow for more efficient and effective disinfection of the tissue. A similar arrangement is contemplated which replaces or supplements the suction tube with an ozone tube which can direct ozone, often mixed with air or oxygen, to tissue near the endoscope.

The lens assembly 15 of FIG. 3 comprises a convex lens 35 and/or concave lens 36 each of which may be independently movable as connected by arm 37. The lens assembly 15 may have multiple lenses of different types, as well as reflectors, to efficiently focus, magnify, and align the UV light coming from the light 18 or produced at the end of light 18 by a chip or LED. Such lens assemblies 15 may be an afocal assembly operating to, for example, collect light using the convex lens 35 and then align the light in an afocal beam using the concave lens 36, or changing the lens assembly, through a control system from outside the body, so that the lens assembly behaves as a concave or convex lens.

Figure 4:
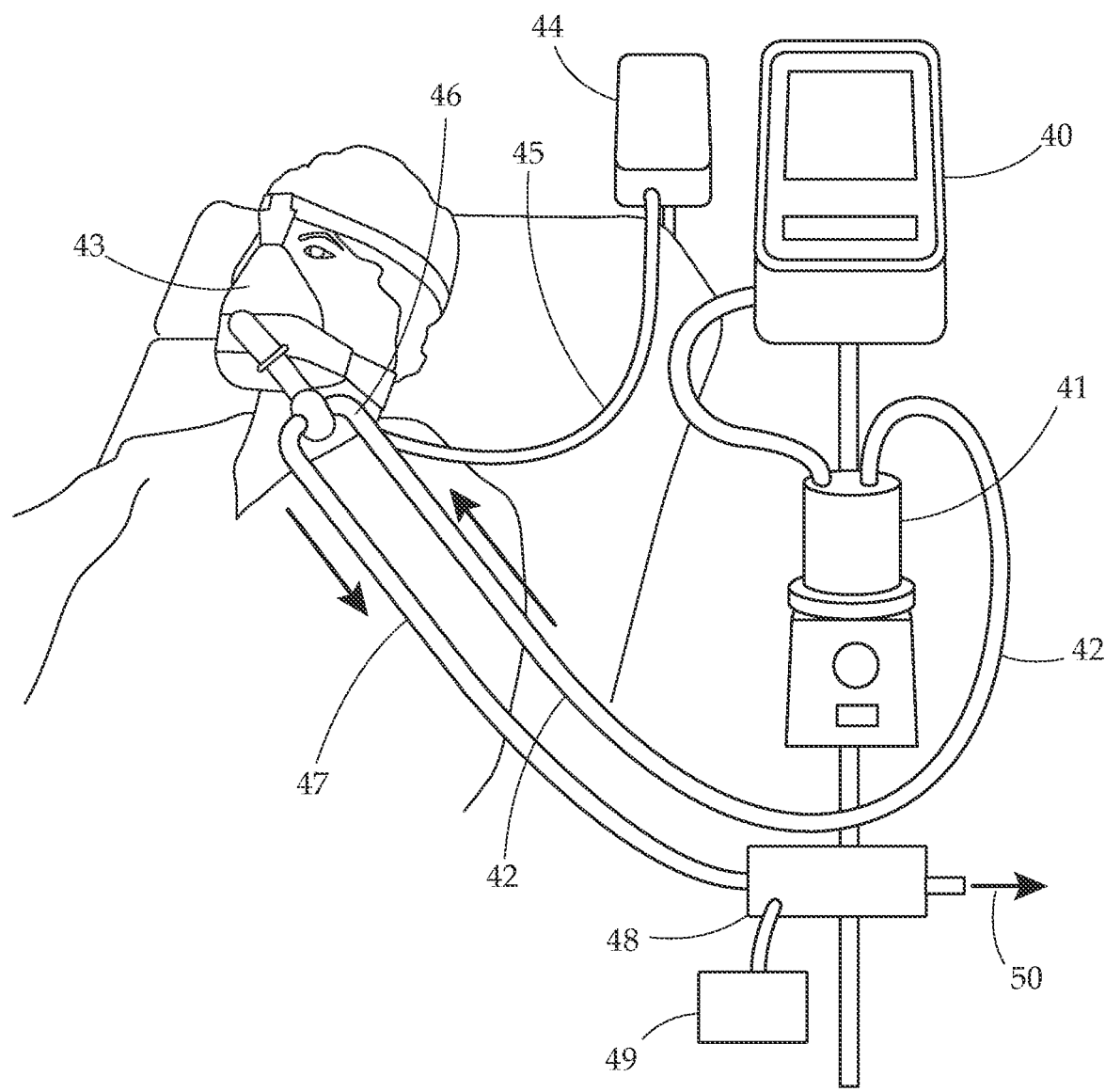
FIG. 4 provides a perspective view of yet another embodiment of the present invention.
Figure 5:
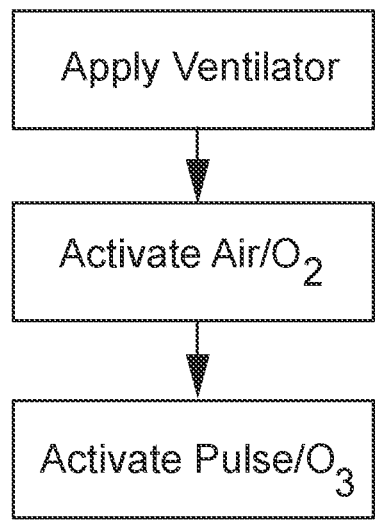
FIG. 5 provides a flow chart of an embodiment of the present invention.
Figure 6:
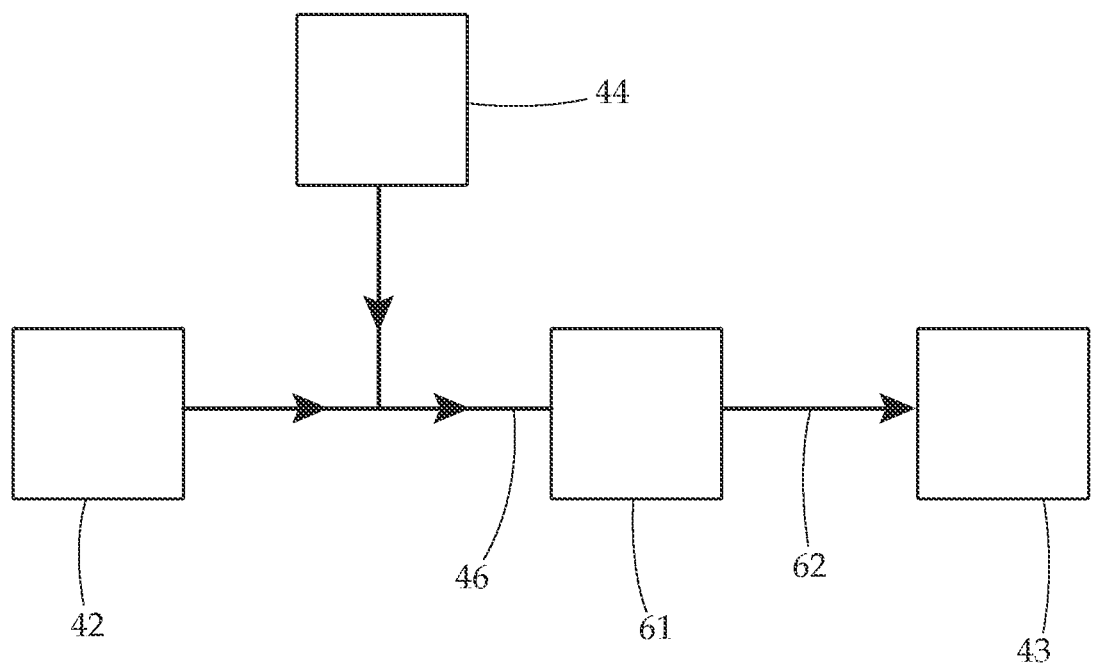
FIG. 6 provides a schematic view of an embodiment of the present invention.

Turning now to FIG. 4, a ventilator providing a disinfecting ozone flow is shown. FIG. 5 provides a flow chart of an embodiment of this system's operation, and FIG. 6 provides a schematic view of another embodiment of the ventilator with ozone disinfection. As noted above, this system may be used as a standalone disinfection system, or may be used in combination with the UV light disinfection endoscope discussed above, either one after the other, or simultaneously.

The ventilator has a controller 40 which pumps and otherwise controls air flow at a controllable rate and schedule to breathe for the patient or provide supplemental air/oxygen flow. This flow will be referred to air flow 42 for simplicity, but may be various combinations of air/oxygen. Air flow 42, which is all or part of the inspiratory flow, passes through humidifier 41 to moisturize the air, and in some cases warm it. The air flow 42 passes through a hose and to, in this embodiment, a face mask 43. Along the air flow 42 path, an ozone flow 45 joins the air flow 42 via hose. Downstream of the ozone joining the air flow is the mixed disinfecting inspiratory flow 46 comprised of the air flow 42 and ozone flow 45. In one embodiment, the ozone tube will be of a different color and/or size than the air flow tube 42 as a safety feature to prevent accidental mix up of the air flow 42 and ozone flow 45. Ozone source 44 provides the ozone flow 45. The ozone source 44 may be an ozone generator, among other options. The ozone source 44 also has a control valve which starts and stops flow of the ozone based on a programming, sensor readings, or a combination of the two. In this embodiment, expiratory gas 47 from the patient is disinfected. This occurs at disinfection unit 48 which, in this embodiment, comprises a UV light which irradiates the expiratory gas 47, as well as an ozone flow 49 to provide further disinfection. Other embodiments may use only one of the UV and ozone disinfection. Outlet air 50 may then be safely vented to the atmosphere or recycled into the ventilator controller 40.

FIG. 6 provides another view of yet another embodiment of the disinfecting ventilator system. In this view, inspiratory air flow 42 is mixed with ozone from ozone source 44 to form disinfecting inspiratory flow 46. This disinfecting flow 46 is even further disinfected by passage through a UV disinfecting unit 61 which exposed the flow 46 to UV light, to ensure that no pathogens enter the patient's lungs. This disinfecting flow 62 is then passed to mask 43 or other inlet structure for the ventilator (nasal tube, intubation, and the like).

Figure 7:
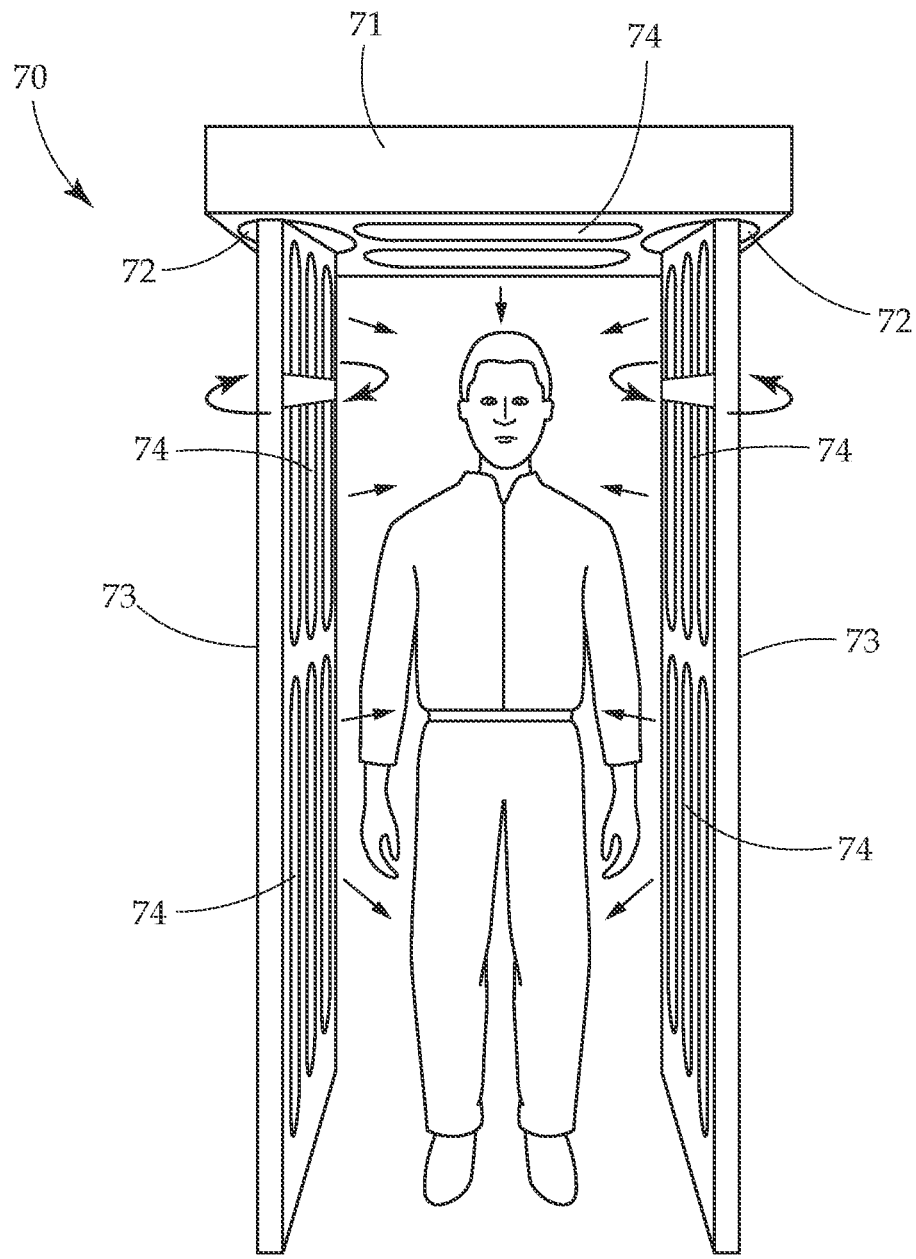
FIG. 7 provides a perspective view of yet another embodiment of the present invention.
Figure 8:
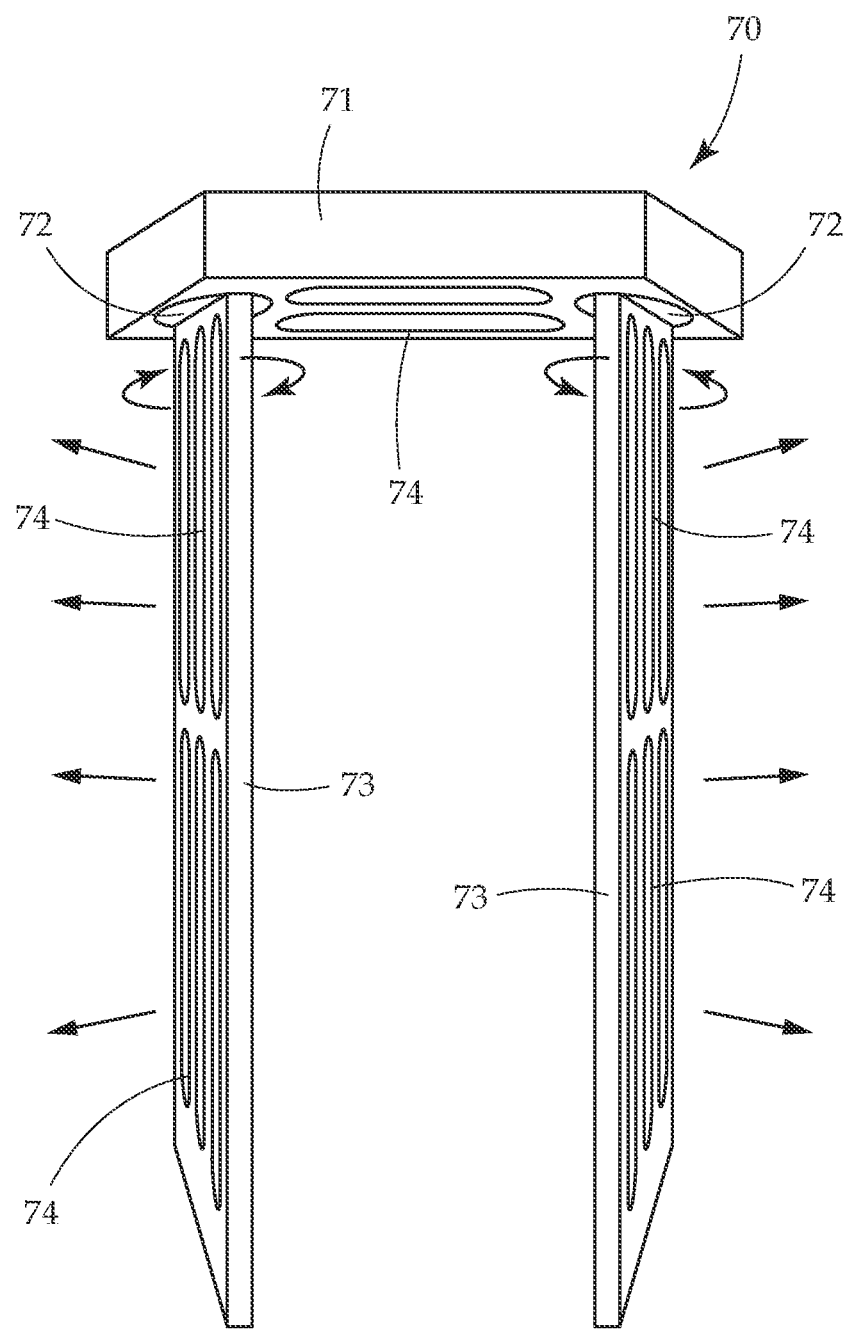
FIG. 8 provides a perspective view of another embodiment of the present invention.

FIGS. 7 and 8 provide a view of a disinfecting passageway which uses UV light to disinfect surfaces, specifically people and their clothes, hair, and the like, passing through. In many embodiments, similarly to the above disinfecting systems, the UV light may be selected to have a particular wavelength(s) known in the art which does not damage human tissue, including skin, eye tissue, and internal tissue, but is lethal to pathogens such as viruses, bacteria, and fungi. In this embodiment, a disinfecting passageway system 70 forms a rectangular or concave passageway via straight or curved side walls 72 and top 71. These are sized approximately similarly to conventional metal detectors, and in some embodiments have a longer passageway, larger space to increase residence time. In any event, the passageway 70 must be large enough for persons of average size to pass through under the top 71 and between the side walls 72. Within the top 71 and sidewalls 72 are one or more UV lamps 74 which provide UV light downward from the top and outward from the front face 73 of the sidewalls 72. One or more mirrors may be used to reflect and direct the light outward towards the front face 73. The mirrored walls are to multiply and magnify the UV light directed to the center of the passageway. The disinfecting passageway 70 may be placed at an entrance to any building or area so that when a user passes through, he or she is disinfected. Examples may include, but are not limited to hospital entryways, doctor's offices, building entry points and exits, airport entrances, and entrances to airplanes or secure areas at an airport, entrances and exits at public transportation stations and public transit vehicles, office building entry/exit, residential entry/exit, and the like, among many other options. In the embodiment shown, the front face 73 of the sidewalls 72 is formed having an arced shape, so that an approximately 120-180 degree UV light arc is provided. Of course other shapes may be used depending on embodiment, including a flat face. Further still, in the embodiment of FIG. 8, the sidewalls 72 are rotatable so that they can be directed outward to disinfect an area surrounding the disinfecting passageway 70. This mode of use can be used overnight or during off-hours when the passageway 70 is not being used to disinfect those passing through it. Rotation may be motorized, manual, spring loaded, and the like. In one embodiment, the sidewalls 72 may be rotatably connected to a central shaft or support which passes all, or partway through the side walls 72. The sidewalls can pivot about this element along a major axis, so as to move between the inward and outward facing positions. Of course, any structure which allows the side walls 72 to rotate so that the front face 73 faces both inward and outward is contemplated therein. In this particular embodiment, eye protector 75 is positioned approximately eye level on the front face 73, so as to limit direct UV light impacting the user's eyes. Eye protection may be used or provided in different embodiments. For example, before entering the passageway, a box of disposable dark eyeglasses (not shown) may be available for people to use.

Figure 9:
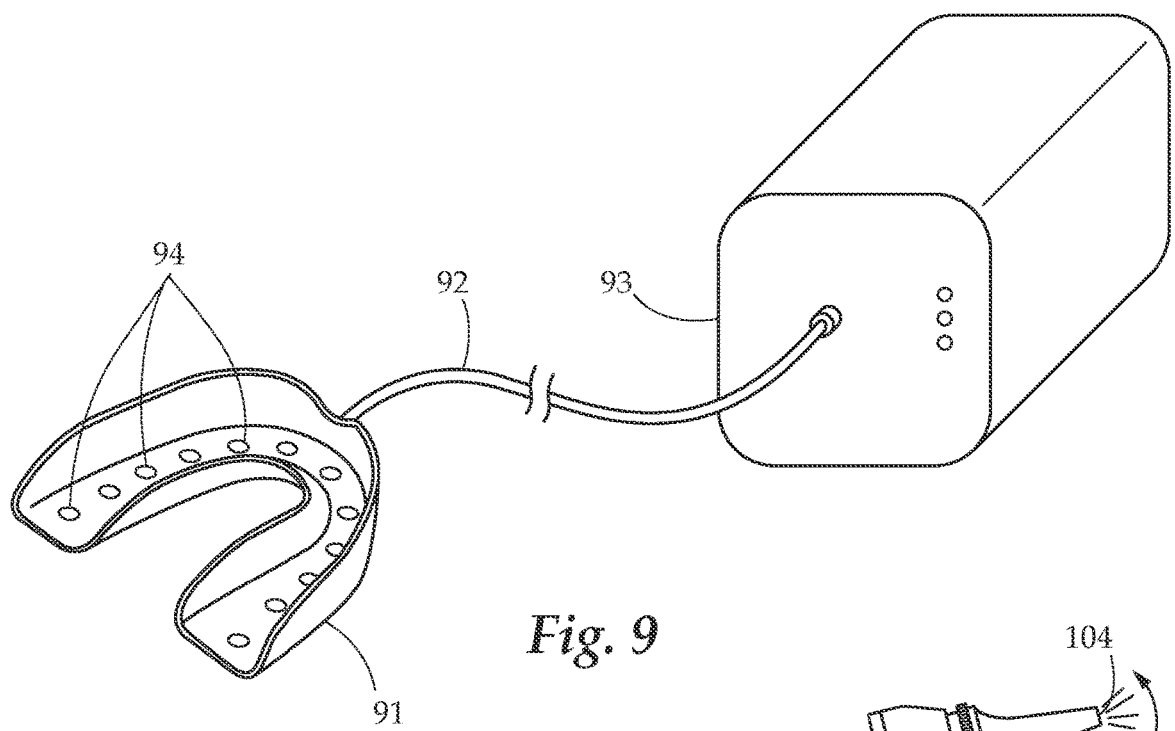
FIG. 9 provides a perspective view of still yet another embodiment of the present invention.

FIG. 9 provides a perspective view of another embodiment of this disclosure. This view provides an aspect of the invention which utilizes UV radiation to disinfect the mouth. A mouthpiece 91 is equipped with one or more UV light sources, show in this embodiment as a plurality of UV LED's 94. In other embodiments, fiber optics and/or the mouthpiece material may be used to direct UV light outward from the mouthpiece 91. In operation, the mouthpiece 91 is placed in a user's mouth and oriented over the teeth of a user. In other embodiments, a user's gums may be covered or enveloped by the mouthpiece 91. Upon, or in some cases before, desired placement of the mouthpiece 91, UV light may be activated by the UV source 94 for a period of time. The amount of time is selected to provide a desirable killing/disinfection/sterilization of the tissue exposed to the UV light from the mouthpiece 91. Plaque, bacteria, viruses, fungi, and other pathogens in the mouth can be destroyed by this treatment. The light may be directed upwards and/or downwards. In some cases, two mouthpieces may be used, each having UV light source 94, with one mouthpiece for the upper teeth and the other for the bottom. Electrical power, in this embodiment, is provided to the UV light source 94 by a power supply 93 and cord 92. In some cases, after a treatment from the UV light source, a user may brush their teeth and/or gums, and/or may rinse with water or another cleansing solution, thereby removing dead tissue and other loosened material, and then further optionally may repeat the UV treatment from the mouthpiece. A battery may be used, for example underneath the light source 94 or otherwise connected thereto, to provide a power source, as opposed to relying on electricity from a wall outlet or power grid.

Figure 10:
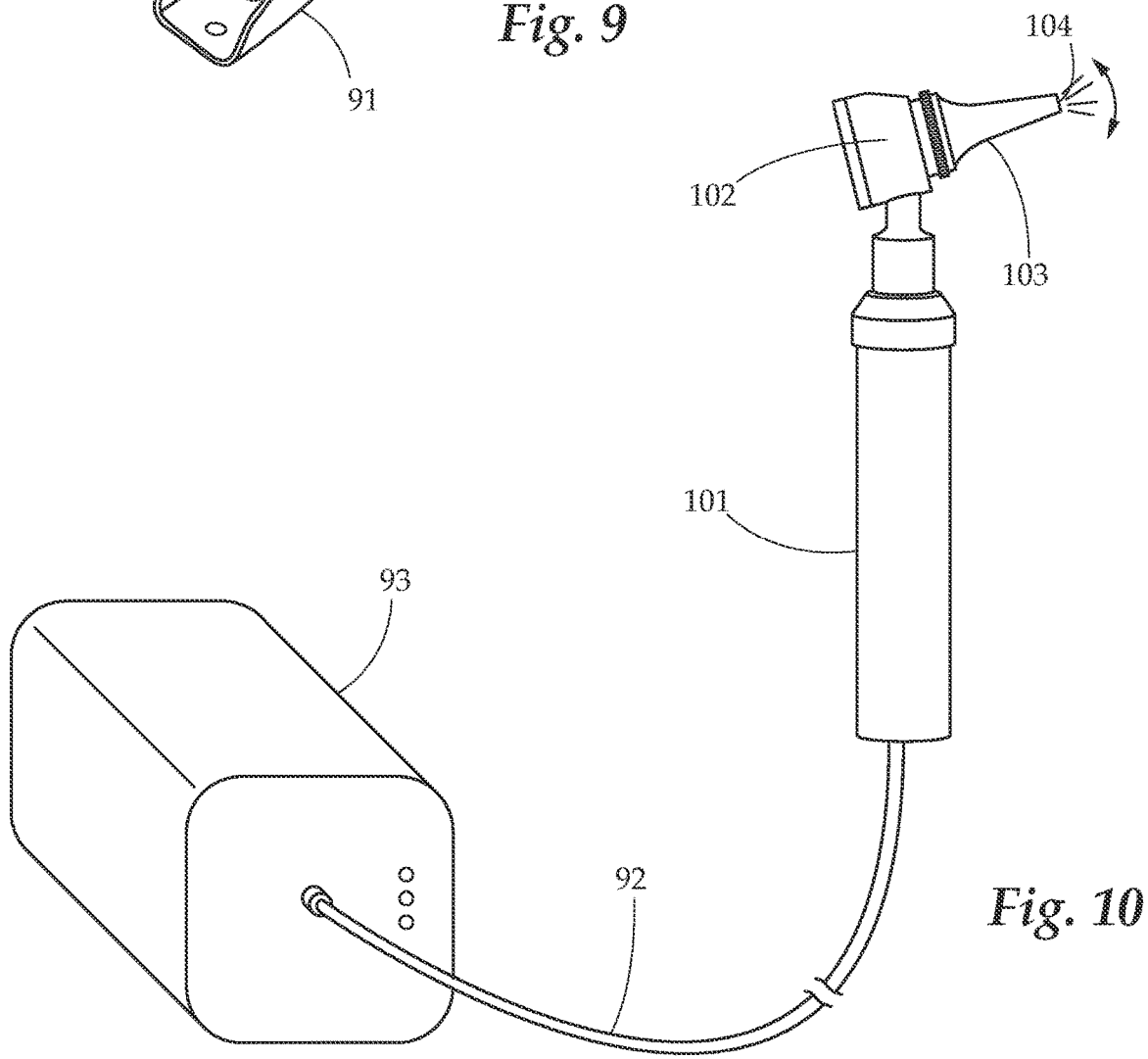
FIG. 10 provides a perspective side view of an embodiment of the present invention.

FIG. 10 provides a view of still another embodiment of the present invention. In this embodiment, a handheld UV source is provided to direct disinfecting UV light to an infected tissue, and/or to tissue susceptible to infection. A pivoting head 102 is connected to a handle 101. At the end 103 of the pivoting head 102 is a UV light source 104 such as an LED or end of a fiber optic cable. The UV light source 104 may be placed into a user's body, such as ears, nose, eyes, mouth, throat, sinuses, and the like. Upon activation, the tissue exposed to the UV light can be disinfected. In this view, a power supply 93 is connected to the UV light source 104 to provide power via cable 92. Of course, battery operated versions of this embodiment may be used as well. As can be understood, the end 103 of pivoting head 102 can be any shape, including an elongate, small and flexible protrusion, able to reach into the desired areas of the body, depending on embodiment. The light source 104 and/or the end of the pivoting head 103 may have systems to focus/direct UV light to the desired location. The UV light may be joined by other light at the end of the tool to illuminate tissue or surfaces with light on the visible spectrum, and further visually explore, view, and treat certain tissue.

Figure 11:
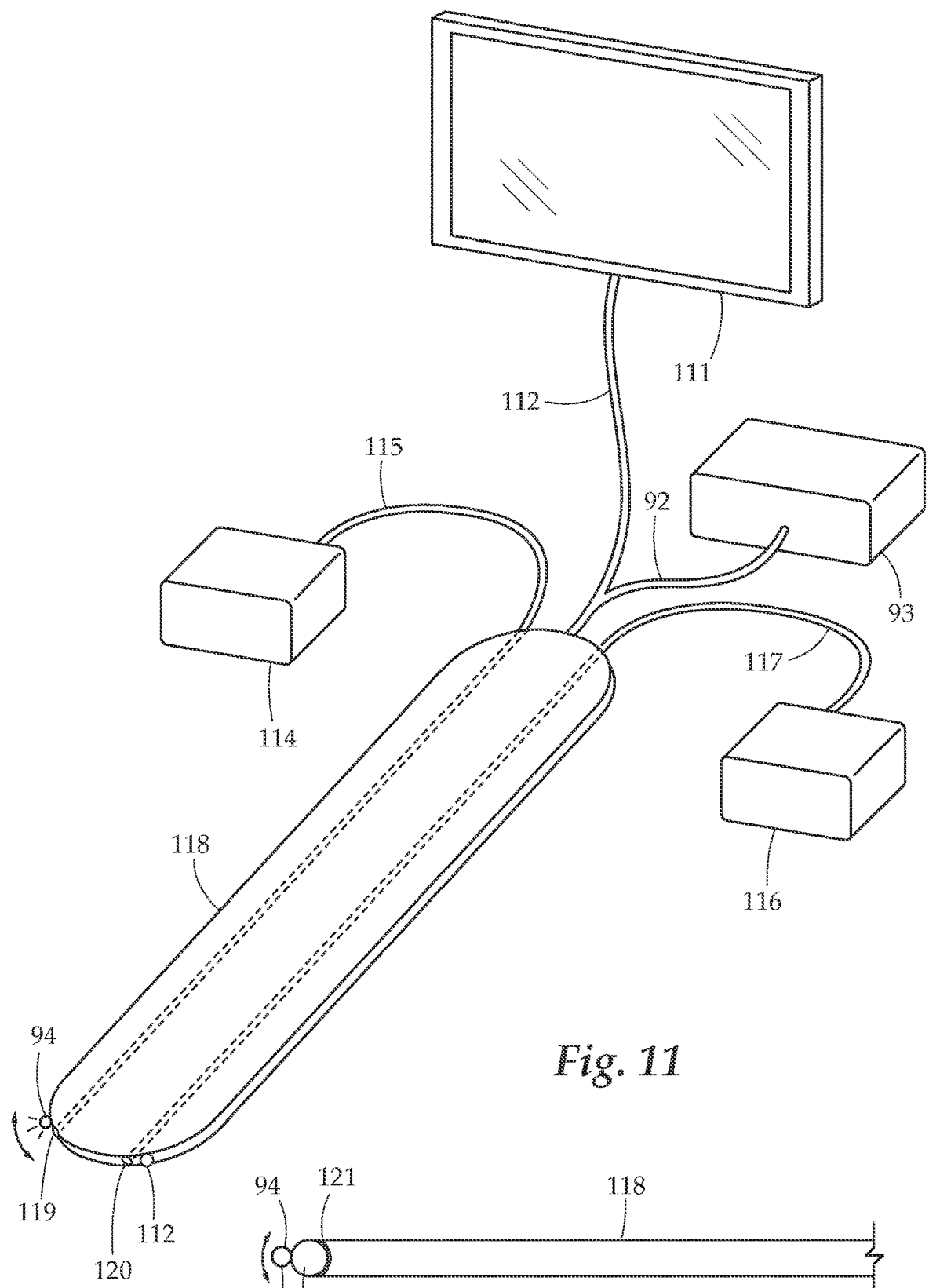
FIG. 11 provides a perspective view of yet another embodiment of the present invention.

FIG. 11 provides a view of yet another embodiment of the present invention. This view provides an embodiment of a tongue depressor stick, or similar elongate and relatively wide tool equipped with a UV light source, camera, a suction tube and a fluid spray tube. The elongate tool 118, in this embodiment, is sized similarly to a tongue depressor having an approximately flat oval and elongate shape. A UV light source 94 such as an LED or end of a fiber optic cable is positioned on the distal end of the tool body 118. A camera 113 is also positioned on the distal end of the tool body 118 allowing an operator to see where the tool distal end is positioned, and to direct the UV light source 94 or other feature of the tool to a desired area. For example, an infected abscess or sore may be targeted by the UV light source 94 and disinfected, as guided visually by the camera informing the operator where to direct the UV light source 94. A display 111 is connected via 112 to the camera 113, allowing the operator to "see" what the camera sees. Similarly, power supply 93 provides electrical power to the UV light source 94 via cable 92. Of course in other embodiments, battery operated systems are also contemplated. The UV light source 94 may be remotely movable relative to the tool body 118 in certain embodiments, while in other embodiments it may be fixed in place relative to the tool body 118. This embodiment of the present invention may be particularly useful for treatment of infected tissue in the mouth and throat.

A suction tube 119 extends through the length of the body 118 to an opening at the distal end of the tool body 118. The other end of the suction tube is connected via tube 115 to a suction source 114 such as a vacuum, a pump, or other similar structure. A spray tube 120 extends through the length of the body 118 to an opening at the distal end of the tool body 118. The other end of the spray tube 120 is connected via hose 117 to a pressure source 116 which provides pressure to spray a fluid or pressurized air. The sprayer tube 120 may operate to clear away dead or extraneous tissue and/or bodily fluids, and may be used either before or after UV light treatment to cleanse the area.

Figure 12:
FIG. 12 provides a side view of the embodiment of FIG. 11.

FIG. 12 provides a side view of one embodiment of the tool of FIG. 11, with this embodiment having an adjustable hinge at the distal end of the body. The hinge 122 is rotatable in socket 121 formed by a concave or recess in the distal end of the tool 118. A camera 112 and UV light source 94 attached to the hinge 122 can in turn be moved up and downwards relative to a plane of the body. This control may be electronic by a motor, or manual by movement of a wire or shaft.

Figure 13:
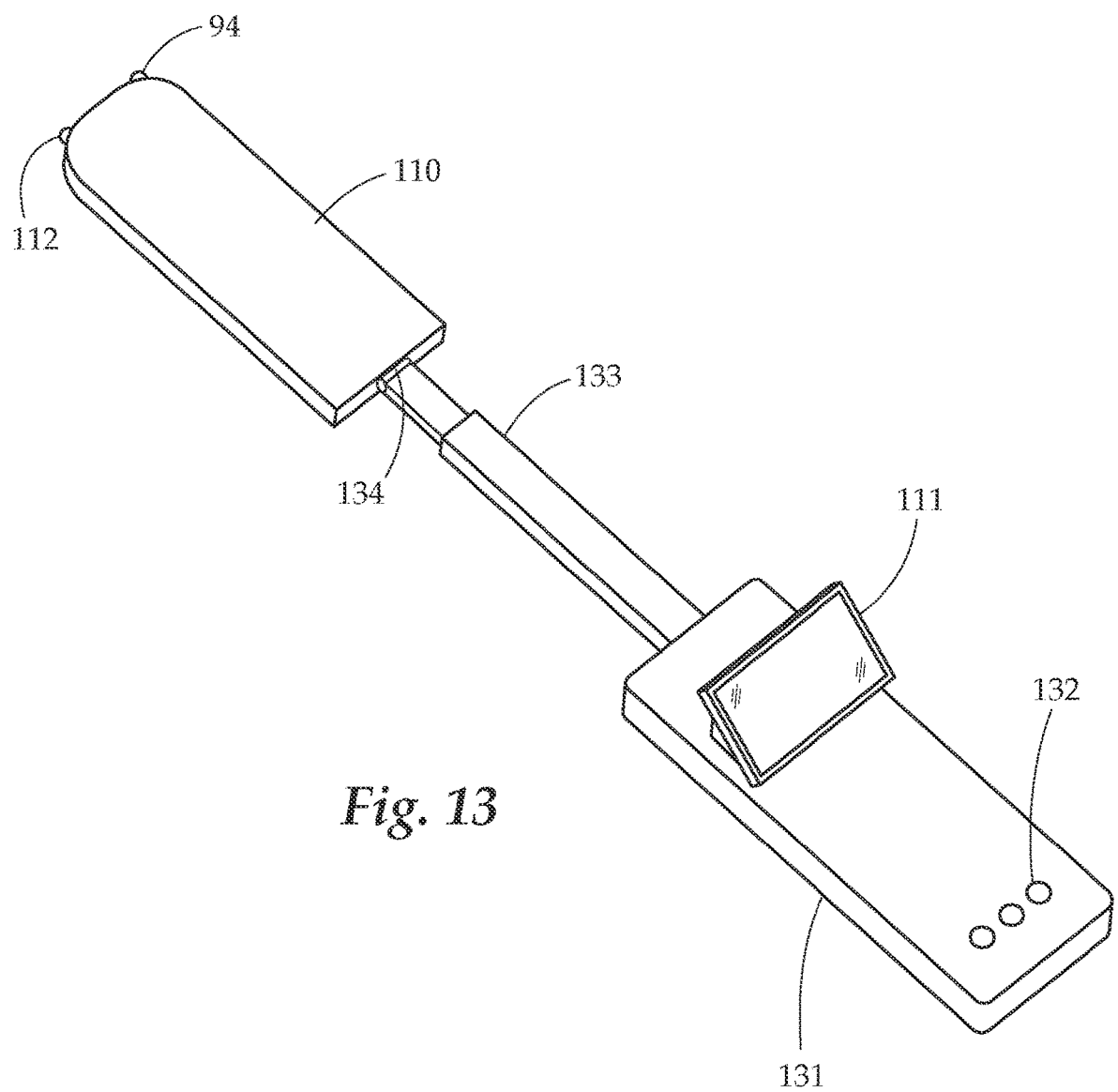
FIG. 13 provides a perspective view of an embodiment of the present invention.

FIG. 13 provides a view of a handheld assembly of the embodiment of FIG. 11. As in FIG. 11, the tool has an elongate and relatively flat and wide tool body 118 having a camera 112 and UV light source 94 attached to its distal end. In this embodiment, the tool body 118 is attached to an extendable and bendable shaft 113 either directly or via hinge 134. At an opposite end of the shaft, a handle 131 allows operation of the device. A plurality of buttons 132 allow control of the tool body 118 including activation and deactivation of the UV light source 94, control of the camera 112, adjustment of the position of the tool body 118, camera 112 and/or UV light source 94 relative to the handle 131, and the like. A display 111 is attached to the handle 131 and is connected to the camera 112 to allow viewing of what the camera is "seeing" and to aid in directing the UV light source 94 to the appropriate area for disinfection. The UV light source may then be activated for a time period to disinfect an area it is directed at such as an infected tissue and/or tissue susceptible to infection.

FIGS. 14-18 provide views of an embodiment of a UV disinfecting curtain which operates to define one or more areas of UV light to act as barriers to pathogens and to fully or partially isolate an area from pathogens and limit pathogen spread. As noted above and referenced in embodiments throughout, certain wavelengths of UV light are highly lethal to pathogens without damaging human tissue. These wavelengths can be used to define disinfecting "curtains" or bars of light which extend across a plane. Any infectious material passing through the light may be killed or deactivated. A plurality of these curtains of light may be used to fully or partially biologically isolate an area, greatly reducing the risk of infection when in public and especially public close quarters. The beams of UV light may be formed in any manner, and in most embodiment define an elongate rectangular cross section of UV light. This light may be reflected in some embodiments to reinforce the light intensity of the UV curtain, or may simply be directed at a surface to be absorbed, reflected/refracted, and otherwise scattered.

Figure 14:
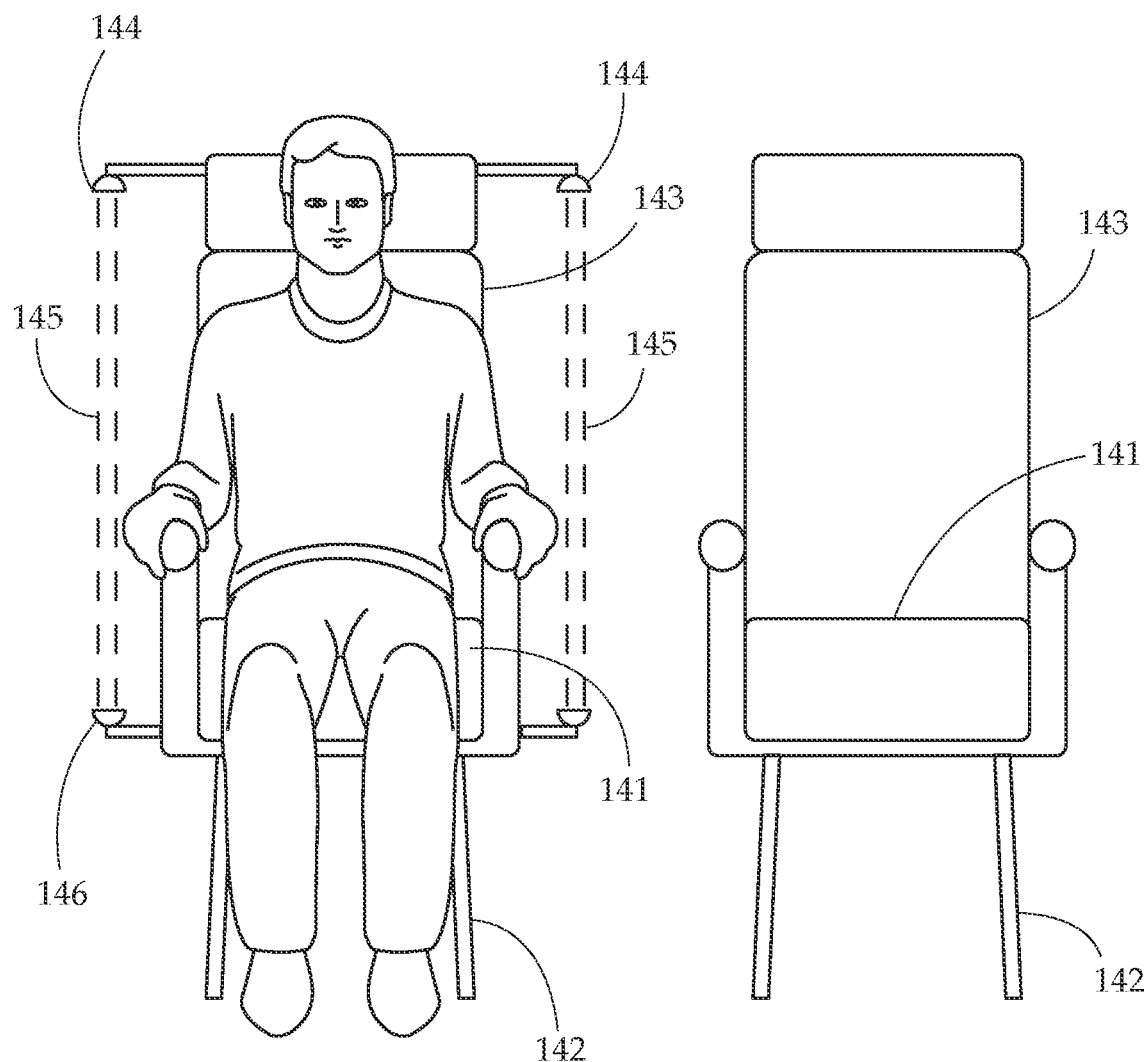
FIG. 14 provides a perspective view of still another view of an embodiment of the present invention.
Figure 15:
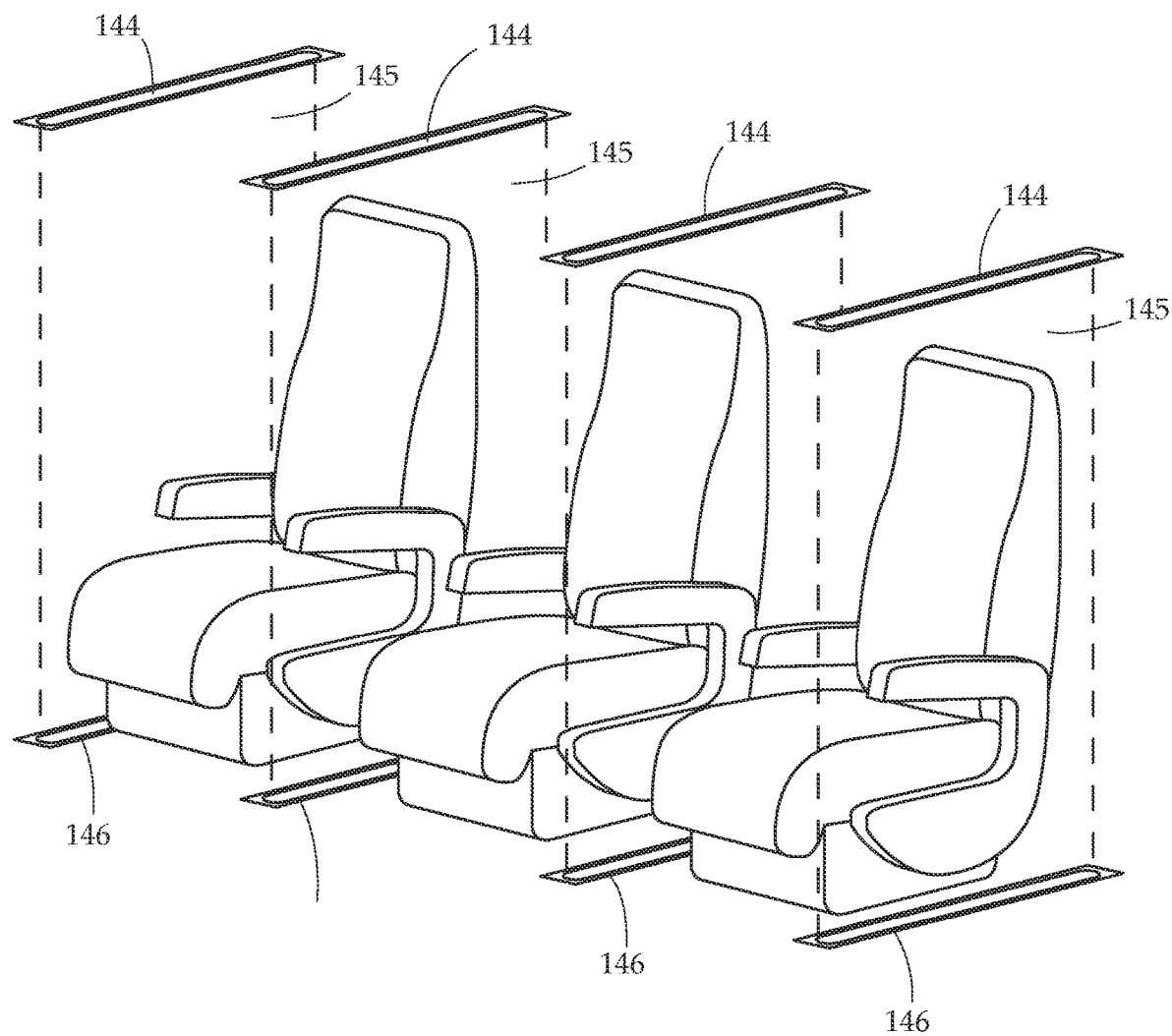
FIG. 15 provides a perspective view of still another embodiment of the invention shown in FIG. 14.
Figure 16:
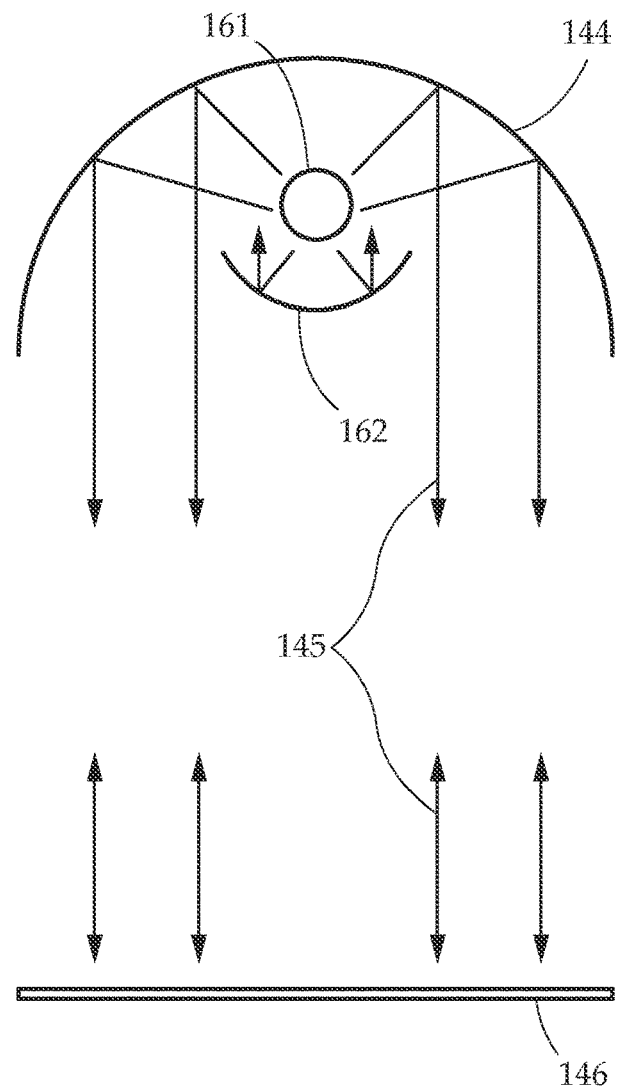
FIG. 16 provides a side view of an embodiment of the present invention.
Figure 17:
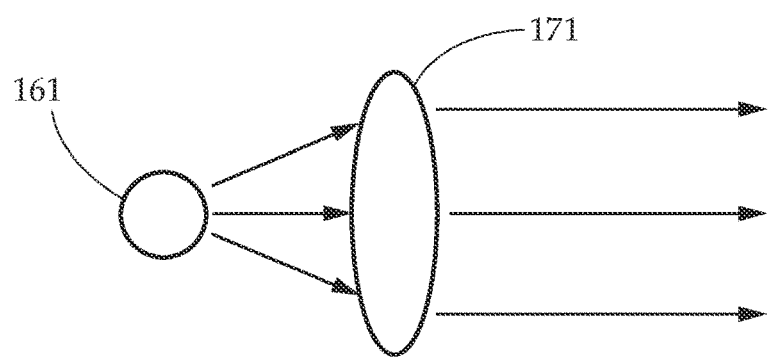
FIG. 17 provides a side view of another embodiment of the present invention.

As seen in FIG. 14, a chair having side UV disinfecting zones, operating as a barrier or "curtains" is provided to limit side to side pathogen transmission over to the second chair. A seat 141 has legs 142 and a back 143. To the left and right of the seat 141 are two UV arrays which provide vertical planar UV light which disinfect any material which passes through them. A top housing 144 is connected at a top of the chair, and a bottom housing 146 is connected near the seat 146. In other embodiments, the bottom housing may go lower and the top housing may be higher. A UV light source (lamp, LED, and the like) in the top housing 144 directs UV light towards bottom housing 146 to form a rectangular planar curtain 145 of disinfecting UV light extending from a rear to a front of the chair, and between top and bottom housings 144, 146. A similar embodiment applied to airplane seats is provided in FIG. 15. To further increase privacy and isolation, a physical curtain may be positioned between the seats to be drawn forward and back. In other embodiments, front, rear, top and bottom disinfecting planes of light may be employed to provide additional isolation from pathogen transmission. In some embodiments, the bottom housing 146 may comprise a mirror which is perpendicular to beams of light coming from the top housing 144 to return the UV light, and thereby increase the intensity of the UV light curtain. In still other embodiments, a UV light source may be positioned in the bottom housing 146 instead of or in addition to the top housing 144. Lenses, mirrors, and apertures may all be used in each of the housings to control, focus, and align the light beams coming from the UV light source. This can be seen in FIGS. 16 and 17. In FIG. 16, A UV lamp or other source 161 is positioned at the focus of a parabolic mirror formed into the top housing 144. A second parabolic mirror 162 is positioned in front of the lamp 161 to direct light back through the focus of the parabola to be directed in parallel as UV light curtain 145. A mirror which is perpendicular to the incoming light 145 is positioned, in this embodiment on the bottom housing 146. In FIG. 17, a lens 171 or plurality of lenses is used to adjust diverging light from lamp 161 to afocal parallel beams.

Figure 18:
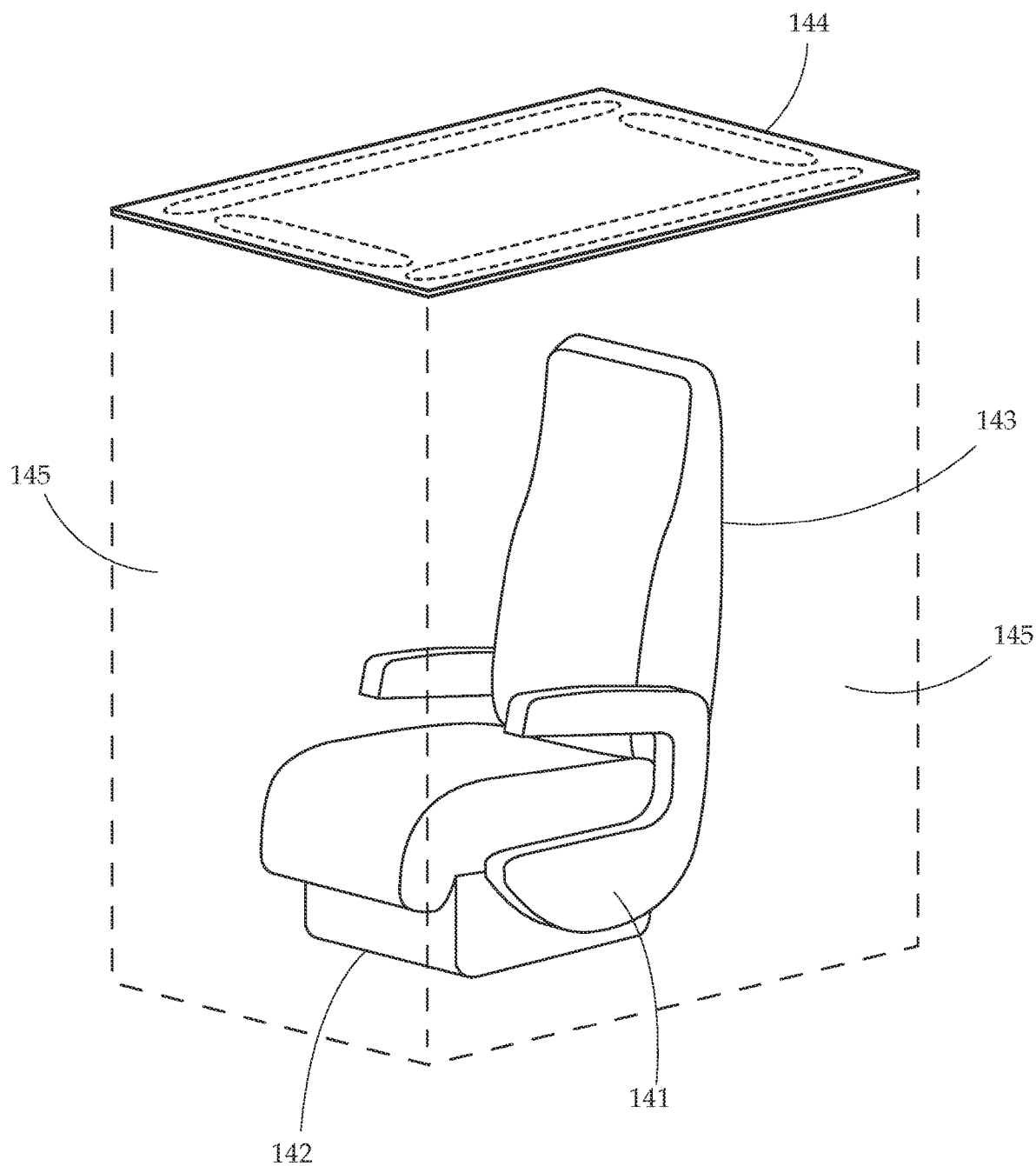
FIG. 18 provides a perspective view of an embodiment of the present invention.

FIG. 18 provides a view of an embodiment of this invention which creates a rectangular UV light plane as a barrier or "curtained" space and covered top to provide full isolation of the interior. In this view, four top housings 144 are formed in a rectangle. In other embodiments, other enclosed shapes of the housing may be used such that the plane of UV light emits from about most or all of a perimeter of the housing. These four top housings direct UV light downward in a curtain 145, as discussed in embodiments above. One or more of the top housings may also be configured to direct a plane of UV light across the area defined by the top housings. As such, the floor, top UV curtain, front, back, and side curtains may combine together to enclose the chair 143 and any person seated thereon. In one particular non-limiting embodiment, this may be used in a hospital to create a "clean" area for a patient, doctors, staff, and the like.

In another embodiment, a suction/vacuum pump, fan, or other air-moving structure may push or draw air into the volume defined by the UV curtain. As the air passes through the UV light, pathogens in the air are weakened, deactivated, or killed. This structure, which can be connected to one or both of the housings or within one or both of the housings, positioned near the housing(s), connected to the chair or other structure that the housings are connected to, positioned within or adjacent to a volume of air protected by the UV light barrier, in communication with the volume of air on an opposite side of the light barrier, or the like. In operation, air that is potentially carrying a pathogen is drawn away from the surroundings of the protected area, and/or removed from within the protected area. This operates to draw away any pathogens, including any weakened, damaged, or destroyed pathogens which have passed through the UV barrier or which may pass through the UV barrier as part of the air flow. This provides a clean air flow into the volume, further enhancing the safety of the area. In a particular embodiment having a suction system in a same housing as the UV light source, one or a plurality of vents may be spaced along the housing so as to efficiently draw air in to remove pathogens as well as dead or damaged pathogens which have been exposed to the UV light. In an embodiment of the housing having a plurality of UV light sources, such as a plurality of lamps or LEDs, vents may be positioned in between the different light sources.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth. Moreover, while certain aspects of the invention are disclosed with certain embodiments, it is to be understood that these different aspects of the embodiments may be combined and interchanged with other embodiments. Indeed by this written disclosure, any element, step, or other aspect of one disclosed embodiment may be equally applied to any other embodiment without straying from the scope of this invention.

What is claimed is:

1. A disinfection system forming ultraviolet light barrier to separate a first area and a second area comprising:
   a UV light source in a housing, the disinfection system configured such that a plane of UV light is emitted from the housing through a narrow opening defined by the housing;
   wherein the first area is defined on a first side of the plane of UV light, and the second area is defined on a second side of the plane of UV light, such that an infectious material passing through the plane of UV light is weakened, deactivated or destroyed; and
   a second housing separate from and spaced apart from the housing, the second housing comprising a mirror which is perpendicular to the plane of UV light emitted from the housing, operable to reflect the UV light back towards the housing, and thereby increase the intensity of the UV light.

2. The disinfection system of claim 1 wherein an opening of the housing defining a cross sectional shape of the plane of UV light.

3. The disinfection system of claim 1 wherein the housing is oriented horizontally.

4. The disinfection system of claim 1 wherein the housing is movable.

5. The disinfection system of claim 1 wherein the housing comprises a mirror assembly to reflect light from the UV light source, and wherein the housing is operable to direct UV light from the UV light source in one direction along a length of the housing.

6. The disinfection system of claim 1 wherein the housing and second housing are attached to a side of a chair, the housing positioned at a top of the chair, and the second housing positioned below the housing at a bottom of the chair, the disinfection system operable to form the plane of UV light as a curtain on the side of the chair.

7. The disinfection system of claim 6 further comprising a top housing, the top housing comprising a UV light source positioned to direct a plane of UV light over a top of the chair, above the chair.

8. The disinfection system of claim 7 further comprising a second top housing opposite to the top housing and aligned with the plane of UV light over the top of the chair, the second top housing comprising at least one of a UV light source positioned to direct UV light in the plane of UV light, and a mirror operable to direct the plane of UV light from the housing UV light source back to the top housing in the same plane of UV light over the top of the chair.

9. The disinfection system of claim 6 further comprising four top housings formed in a rectangle defining the plane of UV light over the top of the chair, at least one of the four top housings comprising the top housing having the UV light source positioned to direct the plane of UV light over the top of the chair, the plane of UV light bounded on four sides by the four top housings.

10. The disinfection system of claim 1 wherein the plane of UV light is afocal UV light.

11. The disinfection system of claim 1 wherein the housing comprises at least one of a mirror and a lens to form the plane of UV light as afocal UV light.

12. The disinfection system of claim 1 further comprising a battery power source to activate the UV light source.

13. The disinfection system of claim 1 wherein the housing is formed as a closed shape to define a closed area, and comprising a plurality of UV light sources, the plane of UV light emitted along a majority or all of the closed shape defined by the housing.

14. The disinfection system of 13 wherein one of the plurality of UV light sources forms a plane of UV light across an opening defined by the housing, so as to further isolate a volume from pathogen infiltration, the volume defined on a bottom by the floor, on a sides by the UV light plane, and on a top by the plane of UV light across the opening defined by the housing.

15. The disinfection system of claim 14 wherein the system is located in a hospital operating room and comprising a hospital bed within the volume.

16. The disinfection system of claim 14 further comprising a suction system adjacent to the UV light source, the suction system operable to draw air out of the volume, the air containing at least one of pathogens, deactivated pathogens, or dead pathogens.

17. The disinfection system of claim 1 further comprising a plurality of housings each containing a UV light source, wherein the plurality of housings are positioned above a floor, and the UV light directed downward towards the floor so as to create an isolated UV curtain surrounding an area on the floor.

* * * * *